United States Patent [19]
Fry et al.

[11] Patent Number: 6,114,149
[45] Date of Patent: Sep. 5, 2000

[54] AMPLIFICATION OF MIXED SEQUENCE NUCLEIC ACID FRAGMENTS

[75] Inventors: Kirk Fry, Palo Alto; James Larrick, Woodside; Albert Tam, San Francisco, all of Calif.

[73] Assignee: Genelabs Technologies, Inc., Redwood City, Calif.

[21] Appl. No.: 07/742,088

[22] Filed: Aug. 2, 1991

Related U.S. Application Data

[63] Continuation of application No. 07/224,961, Jul. 26, 1988, abandoned.

[51] Int. Cl.$^7$ ..................................... C12P 19/34
[52] U.S. Cl. ............. 435/91.2; 435/91.1; 435/91.5; 435/91.51; 435/6; 436/501; 536/23.1; 536/25.3; 935/7; 935/16; 935/17; 935/78
[58] Field of Search ................... 435/6, 91, 91.1, 435/91.2, 91.5, 91.51; 436/501; 536/27, 23.1, 25.3; 935/7, 16, 17, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,734,363 | 3/1988 | Dattagupta et al. | 435/91 |

OTHER PUBLICATIONS

Byrne, B.C., et al., Nucleic Acids Res. 16(9):4165 (1988).
Engelke, D.R., et al., Proc. Natl. Acad. Sci. USA 85:544–548 (1988).
Erlich, H.A., et al., Nature 331:461–462 (1988).
Kwon–Shi, O., et al., J. Biol. Chem. 282(5):2121–2130 (1987).
Liang, W., and Johnson, J.P., Nucleic Acids Res. 16:3579 (1988).
Rougeon, F., and Mach, B., Proc. Natl. Acad. Sci. USA 73(10):3418–3422 (1976).
Verma, I.M., J. Virol. 26(3):615–629 (1978).
Kalendin et al, *Biokhimiia*, 47(11):1785–91 (1982).
Kalendin et al, *Biokhimiia*, 46(9):1576–84 (1981).
Stenesh, J., *Biochem Biophys Acta*, 475(1):32–41 (1977).
Ruttimann et al, *Eur J Biochem*, 149(1):41–46 (1985).
Scharf et al. (1986) Science, vol. 233, pp. 1076–1078.
Gaubatz et al. (1985) Biochim. and Biophys. Acta, vol. 825, pp. 175–187.
Gaubatz et al. (1982) J. Theor. Biol, vol. 95, pp. 679–696.

*Primary Examiner*—Ardin H. Marschel
*Attorney, Agent, or Firm*—Peter J. Dehlinger; Robert H. Benson; Dehlinger & Associates

[57] ABSTRACT

A method of amplifying a mixture of different-sequence DNA fragments which may be formed from RNA transcription, or derived from genomic single- or double-stranded DNA fragments. The fragments are treated with terminal deoxynucleotide transferase and a selected deoxynucleotide, to form a homopolymer tail at the 3' end of the anti-sense strands, and the sense strands are provided with a common 3'-end sequence. The fragments are mixed with a homopolymer primer which is homologous to the homopolymer tail of the anti-sense strands, and a defined-sequence primer which is homologous to the sense-strand common 3'-end sequence, with repeated cycles of fragment denaturation, annealing, and polymerization, to amplify the fragments. In one embodiment, the defined-sequence and homopolymer primers are the same, i.e., only one primer is used. The primers may contain selected restriction-site sequences, to provide directional restriction sites at the ends of the amplified fragments.

17 Claims, 6 Drawing Sheets

AMPLIFICATION OF MIXED SEQUENCE NUCLEIC ACID FRAGMENTS

This application is a continuation of parent application Ser. No. 07/224,961 filed Jul. 26, 1988 abandoned.

FIELD OF THE INVENTION

The present invention relates to methods of amplifying RNA and single- or double-stranded DNA fragments.

REFERENCES

Cathala, G., et al, *DNA* (1983) 2(4):329.
Jackson, D. A., et al, *Proc Natl Acad Sci* (1972) 69:2904.
Lobban, P. E., et al, *J Mol Biol* (1973) 78:453.
Maniatis, T., et al, *Molecular Cloning: Laboratory Manual*, Cold Spring Harbor Laboratory (1982), p. 280.
Nelson, T. et al, *Methods in Enzymology*, Academic Press, NY (1979) 68:41–50.
Roychoudhury, R. E., et al, *Nucleic Acids Res* (1976) 3:101.
Thompson, J., et al, *Anal Biochem* (1987) 303:334.

BACKGROUND OF THE INVENTION

RNA and DNA cloning techniques, in which RNA or DNA fragments are inserted into suitable cloning vectors, are widely used for identifying specific cloned sequences and for expression of the cloned fragments. In a typical cloning method, total RNA is extracted from a selected source, such as a body fluid, cell, or tissue source, and a poly A RNA fraction, representing predominantly messenger RNA (mRNA), is copied to produce double-strand cDNA fragments. The cDNA fragments are then ligated with restriction site linkers, to provide restriction-site ends for cloning into a selected site in a suitable cloning vector. A fragment library formed from the fragments can be used for hybridization to specific probes, and/or for production of specific coded-for proteins or peptides.

Although the above method has yielded a number of impressive successes, it nonetheless has several limitations. First, where the amount of source material is quite small, e.g., $10^3$–$10^4$ cells, the total amount of extracted RNA and resultant cDNA may be too small to produce a library with an adequate, i.e., representative, number of cloned sequences. Secondly, since the duplex fragments have the same linkers at each end, directional cloning in the cloning vector is precluded. Finally, a large percentage of the RNA species are only partially copied, so that many of the library clones are lacking 5'-end coding regions.

There are other biochemical genetics techniques which are also limited by the amount of available nucleic acid material. For example, it is often of interest to compare the RNA species produced by two related sources, to attempt to identify species which are unique to one source or the other. Since the unique species may exist as only a very small fraction of the total material, a relatively large amount of starting material is needed to isolate the unique sequence(s) of interest.

Similarly, where the source material is suspected of containing a disease agent of interest, at very low concentration, it may be impossible to detect the presence of the sequence of interest by conventional cloning or probe hybridization methods.

Recently, a method for amplifying duplex DNA fragments by repeated strand-replication has been described (U.S. Pat. Nos. 4,683,194 and 4,683,202). This method, generally referred to as a polymerase chain reaction (PCR) method, is designed to selectively amplify fragments containing different known sequences in the two fragment strands, using two primers which are homologous to the two different-sequence regions. The PCR method previously described is of course suitable for amplifying specific fragments for which two different sequence-specific probes exist. However, the described method is not intended for or applicable to the problem of non-specifically amplifying fragments in a fragment mixture containing different sequences.

SUMMARY OF THE INVENTION

It is therefore a general object of the invention to provide a nucleic acid amplification method which overcomes many of the problems and limitations associated with low amounts of material in biochemical genetics methods, as discussed above.

One important object is to provide a simple, rapid method for non-specifically amplifying RNA or DNA fragments non-specifically, i.e., without regard to fragment sequence.

It is a more specific object of the invention to provide such a method which allows successful library clone formation from small quantities of RNA, such as that obtained from as few as $10^3$ cells.

Another specific object of the invention is to provide such a method which can produce directional cloning ends on amplified fragments.

The invention is designed for non-specifically amplifying a mixture of RNA or DNA fragments. The fragments are used to form anti-sense strands having a common 5'-end sequence, typically a homopolymeric sequence, and treated with terminal deoxynucleotide transferase (TdT) and a selected deoxynucleoside triphosphate (dNTP), to add a homopolymeric sequence to the 3' anti-sense strand fragment ends. The anti-sense strands are mixed with a homopolymer primer having a homopolymeric binding sequence which is homologous to a 3'-end sequence in the strands, a common-sequence primer which is homologous to the complement of the 5'-end common-sequence, DNA polymerase and all four dNTPs. The fragments are denatured, annealed under conditions of primer attachment to the fragments, and reacted under conditions in which the primed fragments are converted to double-stranded fragments. The denaturing, annealing, and reacting step are repeated until a desired degree of fragment amplification has been achieved.

In one general aspect, the method is used for amplifying duplex DNA fragments, such as genomic fragments obtained from selected cell or tissue sources. Where the fragments to be amplified are relatively short, i.e., less than about 3–8 kilobases, the treatment with TdT adds the same homopolymeric sequence to the 3'-ends of both sense and anti-sense strands. The 5' common-sequence ends are formed by ligating a complementary homopolymer which is homologous to the 3' homopolymeric sequences. The added homopolymer can serve as both the homopolymer and common-sequence primer, i.e., amplification can be carried out by one homopolymer primer.

Where the duplex DNA fragments to be amplified are greater than about 3–8 kilobases, the "anti-sense" strands may be prepared by (a) denaturing the duplex DNA fragments, (b) adding random primers having (i) 3' random sequences effective to bind to complementary sequences of the sense strand, and (ii) common 5' sequences, and (c), under priming conditions, reacting the primed strands with DNA polymerase and all four dNTPs, under conditions which produce copying of the sense strands.

In another general aspect, the anti-sense strands which are amplified are first-strand cDNA fragments produced by reverse transcription of a mixture of RNA species. In the case of poly A RNA species, the anti-sense CDNA strands may be formed by (a) adding an oligo dT primer to the poly A RNA species and (b) transcribing the RNA in the presence of the oligo dT primer, reverse transcriptase, and all four dNTPs. The resulting cDNA fragments, which have a common poly dT sequence at their 5' ends, are treated with terminal deoxynucleotide transferase, to attach the same or a different homopolymer region to the 3' cDNA ends.

The RNA amplification method is also applicable to cDNA duplex fragments derived from RNA species which may be more than about 3–8 kilobase in length. Here the anti-sense strands may be prepared by (a) isolating the RNA species, (b) adding random primers having (i) 3' random sequences effective to bind to complementary sequences of the RNA species, and (ii) a common 5' sequence, and (c), under priming conditions, reacting the primed RNA species with polymerase and all four dNTPs, under conditions which produce first-strand cDNA synthesis.

The resulting cDNA fragments are treated with terminal deoxynucleotide transferase, to attach a desired homopolymer region at the 3' cDNA ends. As above, the anti-sense strands may have the same or different homopolymer regions at their opposite ends.

The method may be used for constructing a cDNA library in which the cDNA fragment inserts are directionally oriented in a cloning vector. Here the homopolymer and common-sequence primers have different 5'-end sequences corresponding to the sequences of selected directional cloning sites in the vector. The amplified fragments are digested with the corresponding restriction endonucleases, and inserted into the vector by standard methods.

Also disclosed is a modified amplification method for duplex DNA fragments, in which only the 3' ends of the fragments are provided with end priming sequences.

These and other objects and features of the invention will become more fully appreciated when the following detailed description of the invention is read in conjunction with the accompanying drawings.

DETAILED DESCRIPTION OF THE INVENTION

I. Amplifying mRNA Species

The method of the invention is useful for amplifying single-strand RNA species, typically messenger RNA (mRNA) species. Methods for isolating mRNA species from tissue, cellular or body-fluid samples are well known. One method involves formation of a vanadyl-RNA complex, extraction of protein with chloroform/phenol, and precipitation with cold ethanol. In a second method, the RNA is extracted from a guanidium isothiocyanate mixture with phenol, followed by a chloroform:isoamyl alcohol extraction, and precipitation of RNA from the aqueous phase with cold ethanol. The reader is referred to Maniatis, pp. 188–198, and references cited therein for details. One preferred RNA isolation method is described in Cathala.

Most eukaryotic mRNAs are characterized by a 3' terminal poly A sequence which allows isolation by affinity chromatography, using oligo dT bound to a solid support. In addition, or alternatively, total isolated RNA can be further fractionated by density gradient centrifugation, or agarose gel electrophoresis, to obtain a desired size fraction of RNA species.

A. Amplification of Oligo dT Primed cDNAs

In this embodiment of the method, poly A mRNA species are used to produce first-strand anti-sense CDNA strands having an oligo dT 5'-end common sequence and a homopolymeric 3'-end sequence. The method is applicable to amplifying RNA species having a 3' poly A region, and preferably with sizes less than about 3–8 kilobases. In one embodiment, the fragment amplification reaction is carried out in the presence of different-sequence primers, allowing for the production of amplified fragments with directional cloning ends. In another embodiment, amplification uses same-sequence primers, i.e., only one primer.

1. Different-Sequence Priming

Figure 1:
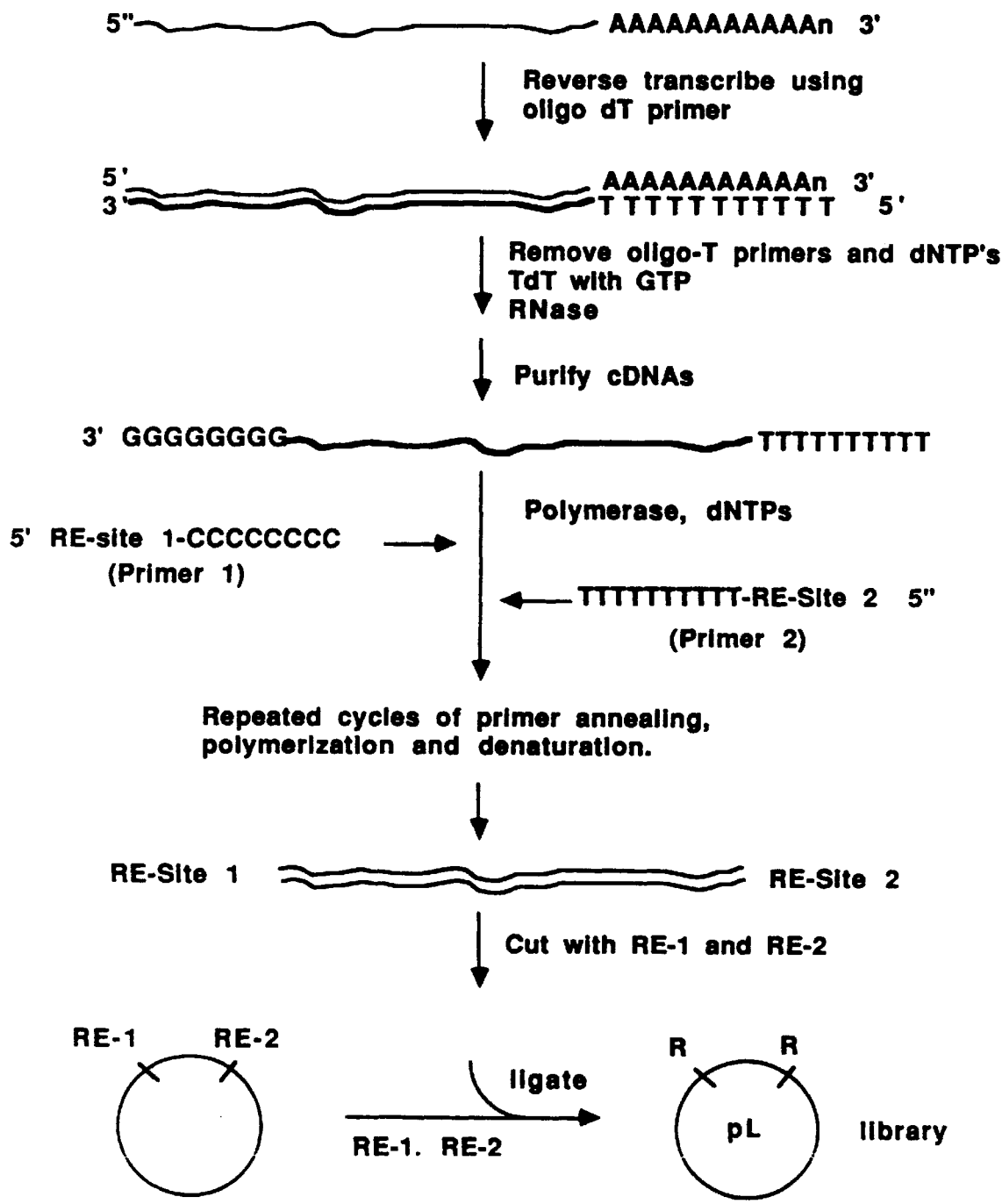
FIG. 1 is a flow diagram of a method for amplifying cDNA produced by oligo dT priming of poly A RNA.

As a first step in the method, the poly A-containing RNA (poly A RNA) species are copied by reverse transcription to form the corresponding first-strand anti-sense cDNA strands. The first-copy synthesis is carried out conventionally using an oligo dT primer in the presence of reverse transcriptase and the four deoxynucleoside triphosphates (dNTPs). As seen in FIG. 1, the anti-sense cDNA strands formed have a 5'-end poly dT region. The duplex fragment mixture is treated to remove oligo dT primer and the dNTPs, for example, by one or more phenol or ammonium acetate precipitation steps, and gel filtration.

After removal of primers and dNTPs, the resulting cDNA fragments, either before or after digestion of the RNA strand, are reacted with terminal deoxynucleotide transferase (TdT) in the presence of a selected dNTP, to form a homopolymer region at the 3' cDNA ends. In the embodiment illustrated in FIG. 1, for directional cloning amplification, the homopolymer is preferably poly dG or poly dC, and the homopolymer tailing reaction is performed with RNA/cDNA duplex fragments. Methods for homopolymer tailing have been reported (Jackson; Lobban; Nelson).

If the RNA strand is present, the efficiency of the reaction can be enhanced by initial digestion with a 5' exonuclease, to expose the 3' fragment ends, or by carrying out the reaction in the presence of cobalt ions (Roychoudhury).

The reaction is carried out under conditions which place at least about 10 and preferably 15 or more bases at the 3' fragment ends. The reaction described in Example 1, which yields poly dG tailing, is exemplary. If the tailing reaction is performed with RNA/cDNA fragments, the duplex fragments are next digested with RNase to remove the sense-strand RNA, yielding single-strand anti-sense strand cDNAs containing a 5'-end oligo dT region derived from the poly A primer, and a homopolymer tail, e.g., dG, at the 3' fragment ends. The RNase, TdT and selected dNTP are removed, for example, by cDNA fragment precipitation.

Since homopolymer tailing by TdT is effective with both single-strand and double-stranded material, the RNA strands in the RNA/cDNA duplex fragments can be removed by RNase digestion prior to homopolymer tailing. One advantage of homopolymer tailing applied to the mRNA/cDNA fragments is that the tailing method selects for full-copy cDNA fragments. This is because the terminal transferase reaction with duplex fragments requires that the 3'-end of the cDNA be substantially coterminous with or longer than the 5' end of the RNA strand. Thus a partially copied cDNA will underhang the RNA strand andnot be tailed efficiently. As a result, the strand will not be amplified.

For amplification, the anti-sense CDNA strands from above are mixed with a homopolymer primer which is homologous to the 3'-end homopolymer tail of the cDNA strands. As used herein, the term "homologous" means that the primer is effective to prime by base-pair specific attachment the 3' homopolymeric region of a DNA strand, under the annealing conditions employed. Typically, the primer sequence is the exact complement of the primer strand region, although variations in sequence correspondence may be allowed, particularly for longer primer sequences. In the embodiment illustrated in FIG. 1, where the homopolymer is poly dG, the homopolymer primer has a homologous poly dC region, containing preferably a run of at least about 15–20 dC bases. It is noted that homopolymer regions in the figures generally contain more homopolymer subunits than actually shown.

Where the amplification is intended to produce fragments for cloning, the homopolymer primer preferably includes at its 5' end, the sequence of a selected restriction endonuclease site, indicated as RE-1 in FIG. 1. This site may be protected by additional 5'-end bases, such as a pair of dG bases.

It will be appreciated that initial replication of the anti-sense strands, using the homopolymer primer, yields complementary sense strands whose 3' end regions are the complement of the common sequence formed at the 5' ends of the anti-sense fragments. In FIG. 1, for example, where the common sequence is poly dT, the complement to this region is poly dA at the 3' ends of the sense fragments. The amplification mixture further includes a common-sequence primer having a sequence which is homologous to the complement to the common-sequence region. The common-sequence primer includes a poly dT region in the FIG. 1 example. Where the primer is used for directional cloning, also includes a 5-end sequence corresponding to a second selected restriction site RE-2 which is different from RE-1. As above, this RE-2 sequence is preferably protected by added 5'-end bases, such as a pair of dGs.

Synthetic single-strand oligonucleotide linkers having selected sequences can be prepared using commercially available automated oligonucleotide synthesizers. Alternatively, custom designed synthetic oligonucleotides may be purchased, for example, from Synthetic Genetics (San Diego, Calif.).

An exemplary homopolymer primer having a 5' XbaI site and a common-sequence primer having a 5' XhoI site are shown at A and B below, respectively:

(A) d(5'-GG<u>TCTAGA</u>C$_{20}$-3')
       <u>XbaI</u>

(B) d(5'-GG<u>CTCGAG</u>T$_{20}$-3')
       <u>XhoI</u>

The anti-sense cDNA strands from above are amplified by repeated fragment duplication according to the following steps. First, the fragments are denatured, preferably by heating, and mixed with a molar excess of the homopolymer primer and common-sequence primer described above. As noted above, the primer sequences and lengths are such as to allow primer attachment to the 3'-end homopolymeric regions of the sense and anti-sense strands, sufficient for DNA polymerase priming. Another requirement is that the primer, when attached to the linker region of the denatured fragment strands, be capable of priming polymerase-catalyzed strand replication; that is, that the internal end of the primer provides a free 3'-OH.

The denatured fragments are then annealed, preferably by cooling, such as to between about 37–60° C., to allow homopolymer primer attachment to the anti-sense cDNA fragments. The four dNTPs and a DNA polymerase capable of catalyzing second-strand primed replication are added, and the reaction mixture is brought to a temperature suitable for enzymatic strand replication.

In the method described in Example 1 below, the dNTPs and DNA polymerase were added prior to fragment denaturation. After heat denaturing, the mixture was annealed at 50° C. for two minutes, then brought to 72° C. for 5–12 minutes for primed, second-strand replication. The DNA polymerase used was *Thermus aguaticus* DNA polymerase (Taq DNA polymerase), which is relatively heat-stable at up to 95° C. for brief periods.

It will be appreciated from the above, and from FIG. 1, that the homopolymer and common-sequence primers are effective to prime the 3'-end homopolymer regions in each DNA strand, and thus a doubling of fragment number occurs at each replication. The above replication procedure, which involves fragment denaturation, annealing to allow primer attachment to form strand-primer complexes, and second strand replication of the complexes in the presence of DNA polymerase, is repeated until a desired concentration of fragments is achieved. In the above example, which employs a heat-stable <u>Taq</u> polymerase, the replication steps are carried out by heating the fragment mixture to a denaturing temperature (above the $T_m$ of the fragments), cooling briefly to allow fragment/primer complex formation, and incubating for a period sufficient for second-strand synthesis. The period of incubation for the polymerization may be extended up to about one-half hour for longer fragments, e.g., up to 8 kilobases in length.

Since the concentration of fragments doubles at each round of replication, a $10^3$ fold amplification can be achieved with about 10 rounds of replication, and a $10^6$ fold amplification with about 20 rounds of replication. Thus, initial picogram amounts of RNA species will yield microgram amounts of fragment material after about 20 rounds of replication.

Following the DNA amplification procedure, the fragments are separated from the polymerase and polynucleotide components, typically by phenol extraction.

Example 1 illustrates the application of the amplification method to a mixture of poly A RNA species isolated from human peripheral blood T cells. As demonstrated by the gel patterns in FIG. 7, the method is effective to generate detectable amounts of duplex DNA from RNA isolated from as few as $10^3$–$10^4$ cells.

The lower portion of FIG. 1 illustrates how the amplified fragments may be directionally cloned into a suitable cloning vector. The procedure is described in Example 1, where the RE-1 and RE-2 sites indicated in FIG. 1 are the rare fragment-end restriction sites XbaI and XhoI, respectively. After amplification, the fragments are digested with with XhoI and XbaI, and inserted into a Bluescrip™ vector having unique XbaI and XhoI sites. Ligation and selection of successful recombinants is conventional.

Preferred vectors for directional cloning contain an RNA polymerase promoter site adjacent the insertion site which corresponds to the 5' end of the amplified RNA. When this vector is cut at the restriction site at the fragment insert end opposite the promoter, and treated with RNA polymerase in the presence of all four dNTPs, the system transcribes RNA strands which can be used by the host for protein production. It will be appreciated therefore that the primer restriction sequences in the amplification method must be selected such that insertion into the vector places the 5' end of the anti-sense strand in the duplex cDNA adjacent the polymerase promoter. Alternatively, the cloning vector may be provided with polymerase promoters at both insertion sites, allowing for sense-strand transcription by cutting the recombinant vector at the fragment end which gives sense-strand transcription.

2. Same-Sequence Priming

Figure 2:
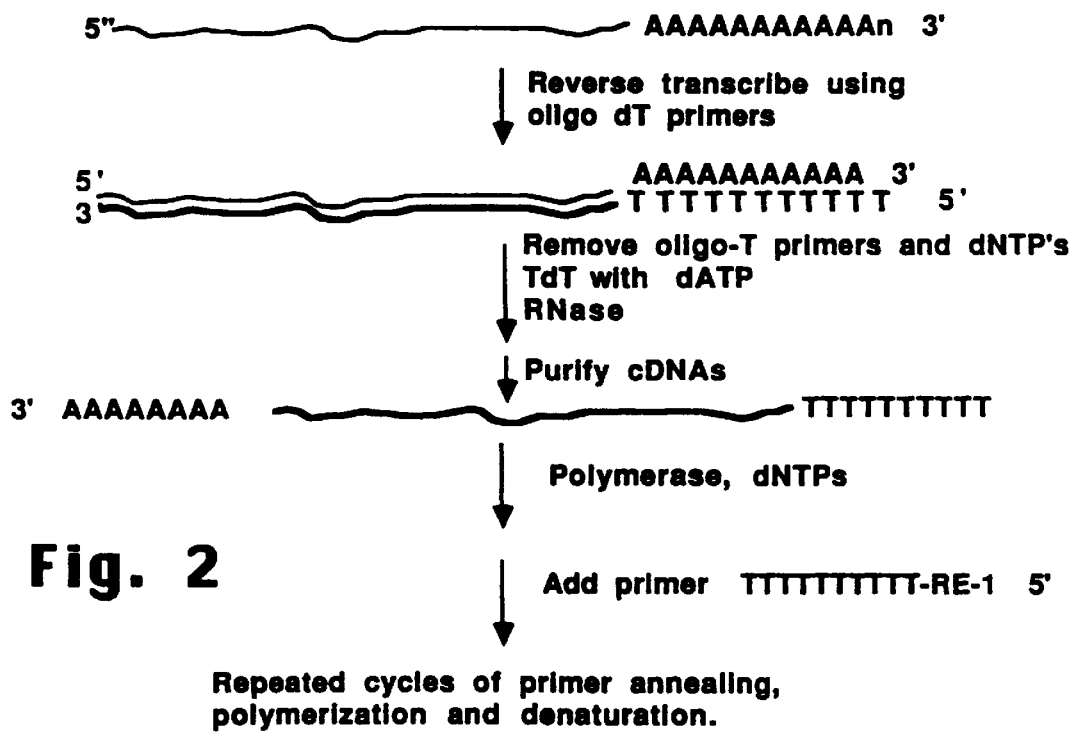
FIG. 2 shows a variation of the FIG. 1 method in which fragment amplification is carried out using same-sequence primers.

In another general embodiment, illustrated in FIG. 2, the anti-sense cDNA strands formed by oligo dT priming are treated to include 3'-end poly dA homopolymeric sequences. The initial step, involving oligo dT priming for first-strand cDNA synthesis, follows the method illustrated in FIG. 1. After removal of reverse transcriptase and the four dNTPs, the RNA/cDNA fragment is treated with TdT and DATP, under conditions described above, to attach a poly dA homopolymer tail to the cDNA 3' ends, as shown.

After digestion of the RNA strand, and removal of terminal tailing components, the cDNA strand is mixed with a homopolymer primer containing a 3' oligo dT sequence and preferably a 5' sequence corresponding to a selected restriction endonuclease site, such as XhoI. One exemplary primer has the sequence:

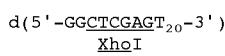

The primer is present in large molar excess with respect to the fragment concentration, and comparable or greater in concentration to the calculated intramolecular strand end concentration to minimize hybridization between the complementary fragment ends, which would form either fragment circles or concatemers. Typically, the primer molar concentration is at least about $10^3$ higher than cDNA fragment concentration and about 1 uM or greater. It may also be necessary to add additional primer during the polymerization reaction mixture, to replenish primer which is used up during the amplification reaction.

It will be appreciated that initially, the newly formed sense strands have a common poly dA sequence at their 3' ends, and that this sequence is also homologous to the homopolymer oligo dT primer. Thus with heating to denature the two strands, and cooling to reanneal the primers, both strands are now primed at their 3' ends. The poly dT primer therefore serves as the homopolymer primer, for priming the anti-sense strand cDNAs, and as the common-sequence primer, for priming the sense-strand cDNAs. Amplification is carried out, as above, with repeated primer annealing, polymerization, and denaturation, substantially as described above, and in Example 1.

Where, as indicated, the homopolymer primer has a selected restriction site sequence RE-1, the amplified fragments will have this restriction site at their opposite ends. The fragments may be cloned in a suitable cloning vector by digesting the fragments with the corresponding restriction enzyme and inserting the digested fragments into a compatible-end site in the vector.

B. Amplification of Random Primed cDNAs

In this embodiment of the method, mRNA species are used to produce first-strand anti-sense cDNA strands having a 5'-end common sequence contributed by random primers, and a homopolymeric 3'-end sequence. The method is applicable to amplifying RNA species which do not have a 3' poly A region, and/or which are greater than about 3–8 kilobases in size, where it is desired to amplify the 5'-end regions of the RNA species. As above, the fragment amplification reaction may be designed to be carried out in the presence of different-sequence primers, allowing for the production of amplified fragments with directional cloning ends, or alternatively, using a single primer.

1. Different-Sequence Priming

As a first step in the method, the RNA species are copied by reverse transcription to form the corresponding first-strand anti-sense cDNA strands. The first-copy synthesis is carried out conventionally using random primers having a 3' random sequence of typically about 4–8 bases, and a 5' region of a common sequence of typically about 15–20 bases. The random primers shown in FIG. 3 have 6 random-sequence bases, indicated by N's, and a common ATCGAGGCTG-RE-2 5' sequence, where the RE-2 sequence typically includes 4–8 bases and a pair of terminal protective bases, as above. The random primers are synthesized conventionally by selecting each of the four bases for each N, e.g., for the first six 3' positions, and selected bases for each of the following positions. Thus, in the case of six N's, the primer mixture theoretically includes $4^6$ primer sequences.

After addition of the random primers, first-strand cDNA synthesis is carried out by addition of reverse transcriptase in the presence of all four dNTPs, as above. As seen, the resulting anti-sense cDNA strands all contain the 5'-region common primer sequence at their 5' ends. Since the random primers will prime the RNA species at at random positions with respect to the RNA 5' end, the cDNA fragments will have variable lengths, of 5'-end sequence. After removing the dNTPs and reverse transcriptase, the RNA/cDNA fragments are treated with TdT and a selected deoxynucleotide, as above, to attach a homopolymer tail to the 3' CDNA ends. As noted above, the homopolymer tailing procedure selects cDNA fragments which are coterminous with the 5' RNA sequence, i.e., which include the 5' end coding region of the RNA species.

The anti-sense fragments are now amplified, as above, by addition of polymerase, the four dNTPs, a homopolymer primer, for priming the 3' end of the anti-sense cDNA, and a common-sequence primer for priming the 3' region of the opposite cDNA sense strand. As above, where the method is intended for directional fragment cloning, each primer includes a 5' sequence corresponding to a selected endonuclease site.

After repeated cycles of primer denaturation, annealing, and polymerization, the amplified fragments are separated from the reaction components, as above. For fragment cloning, the fragments are digested with the fragment-end endonucleases and ligated into a suitable two-site cloning vector as above.

2. Same-Sequence Priming

Figure 4:
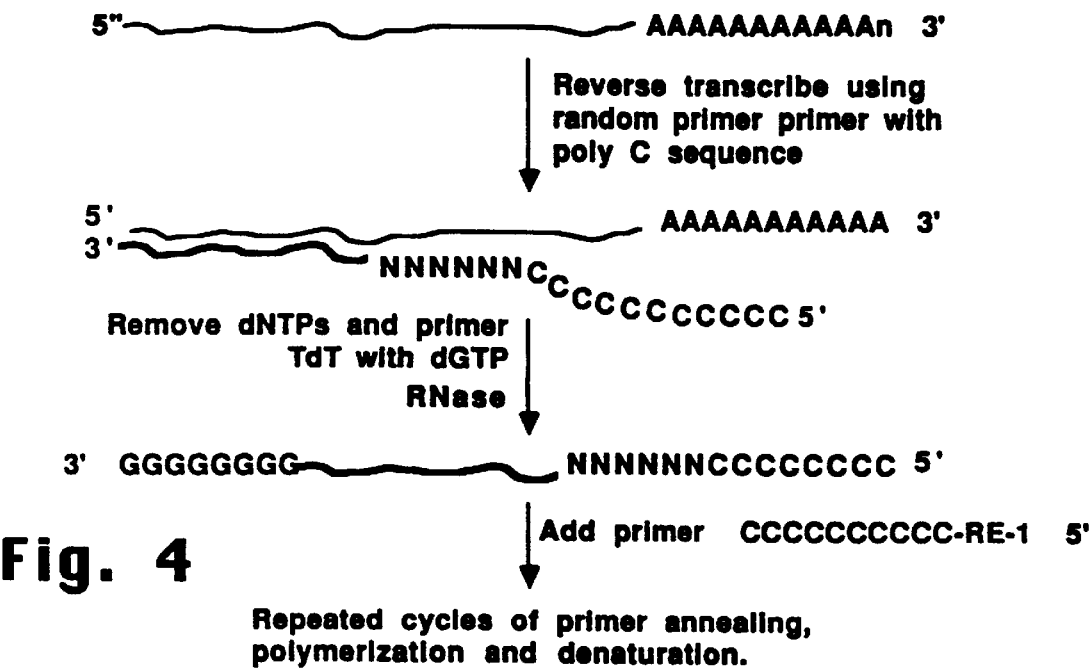
FIG. 4 is a flow diagram of a method like that shown in FIG. 3, but where the first-strand cDNA is primed by a random primer.

This embodiment of the method follows the random primer method discussed in Section IA.2. above, except that first-strand cDNA synthesis is primed by random primers containing a 5'-region homopolymeric common sequence. This method is illustrated in FIG. 4. The upper portion of the figure shows the synthesis of a first-strand cDNA from a poly A RNA, with a random-sequence primer. As illustrated, the primers includes a sequence of six arbitrary bases, designated at N, followed by a homopolymer sequence, e.g., poly dC, and terminating with the sequence of a selected restriction endonuclease, such as XhoI. As above, the restriction-site sequence may be protected by two or more additional bases. If the RNA species include poly A RNAS, the primer homopolymer region should not be oligo dT since primer binding to the poly A region would interfere with the priming reaction. One exemplary primer has the sequence:

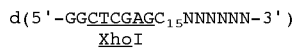

After first-strand CDNA synthesis, the reverse transcriptase reaction components are removed, and the RNA/cDNA duplex fragments are reacted with TdT and a dNTP which is the complement of the primer homopolymer sequence. Thus, where the primer homopolymer sequence is poly dC, as shown in FIG. 4, the homopolymer tailing nucleotide is dGTP. The resulting anti-sense strand cDNAs thus contain a 5' poly dC common-sequence region and a 3' poly dG homopolymer region.

After digestion of the RNA strands and removal of non-fragment reaction components, the cDNA fragments are mixed with a large molar excess of a homopolymer primer, such as a poly dC primer which also preferably contains the sequence of a selected restriction site. Fragment amplification is carried out, as above, in the presence of DNA polymerase, all four dNTPs, with repeated cycles of primer denaturation, annealing, and polymerization. In the specific method shown in FIG. 4, where the homopolymer tailing adds a 3' end poly dG region, the newly formed sense strands have a common poly dG sequence at their 3' ends. The poly dC primer thus serves as the homopolymer primer, for priming the anti-sense strand cDNAs, and as the common-sequence primer, for priming the sense-strand cDNAs.

For cloning, the components are digested with the end-site endonuclease, and inserted into the single site of a suitable cloning vector, as above.

II. Amplifying Duplex DNA Fragments

Single- and double-stranded DNA fragments, either in a fragment mixture or a purified preparation, are also suitable for amplification, according to the method of the invention. Genomic DNA from a selected cell source can be isolated by standard procedures, which typically include successive phenol and phenol/chloroform extractions with ethanol precipitation. The isolated DNA may be obtained from isolated chromosomes or chromosomal regions of interest. The duplex DNA is fragmented preferably by partial or complete digestion with one or more selected restriction endonucleases, although mechanical shearing may be employed. The fragmented genomic pieces may be size fractionated, or further treated to remove repetitive DNA.

Other sources of double-stranded DNA fragments can include extrachromosomal material, e.g., mitochondrial DNA, double-stranded DNA viruses, or viruses which have as part of their life cycle a double-stranded intermediate, e.g., retroviruses.

Cellular sources of genomic DNA fragments or RNA transcripts used for producing cDNA fragments include cultured cell lines, or isolated cells or cell types obtained from tissue (or whole organs or entire organisms). Cell sources are of interest in a variety of subtraction techniques where it is desired to identify or isolate particular RNA transcripts or genomic material which are unique to one of two related cell sources. Body-fluid sources of DNA and/or mRNA transcripts are of interest primarily where the fluid is known or suspected to contain a viral agent or other microbe of interest.

Linearized or fragmented plasmid DNA, or fragmented phage DNA is another source of DNA fragments which one might wish to amplify. The vector DNA is obtained from purified plasmid or phage DNA according to conventional techniques, and linearized and/or fragmented by digestion with selected restriction endonuclease(s).

A. Opposite-End Homopolymer Tailing

Figure 5A:
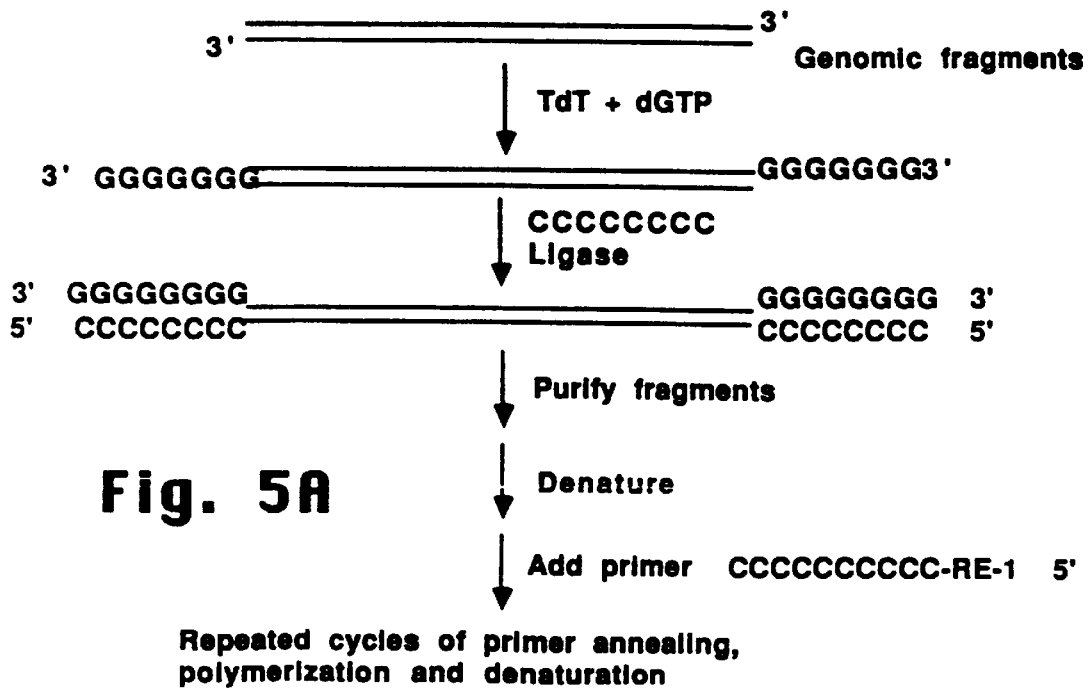
FIG. 5A is a flow diagram of a method for amplifying duplex DNA fragments, according to one embodiment of the invention.

This embodiment of the method, which is illustrated in FIG. 5A, is suited for amplifying duplex DNA fragments less than about 3–8 kilobases long. The fragments, such as the duplex fragment at the top in the figure are reacted with TdT in the presence of a selected dNTP, such as dGTP, to attach homopolymer tails at opposite 3' ends of the fragments, as indicated. Reaction conditions are preferably adjusted to add about 20–40 bases at each 3' fragment strand end.

The tailed fragments are extracted from the reaction components, such as by phenol extraction and gel filtration, and mixed with a molar excess of homopolymers which are complementary to the homopolymer tails. For example, where the homopolymer tailing adds poly dG tails, the homopolymers are poly dC. The homopolymers are preferably at least about 15–20 bases long. The duplex fragments are heat denatured, as above, and annealed under conditions which allow homopolymer hybridization to the 3' homopolymeric fragment ends. The annealed fragments are then treated with T4 DNA ligase in the presence of $Mg^{+2}$ and ATP under standard conditions (Maniatis, p. 146) to ligate the homopolymers at the 5' strand ends of the fragments. The resulting fragments thus have 3'-end homopolymer sequences and 5' end complementary sequences which form the 5' common sequences in the fragment strands.

After fragment purification to remove reaction components, the fragments are mixed with a homopolymer primer which preferably contains the sequence of a selected restriction endonuclease site. One exemplary primer, for use with oligo dG tailing, and for providing terminal XhoI sites, has the sequence:

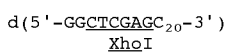

The amplification reaction is carried out as above, with repeated cycles of denaturation, annealing, polymerization, and denaturation. As with single-primer methods described in Section I above, the homopolymer primer serves as both the homopolymer primer for the 3' end sequence of the anti-sense strand, and as the common-sequence primer for the common homopolymer sequence at the 3' ends of the sense strands.

Figure 5B:
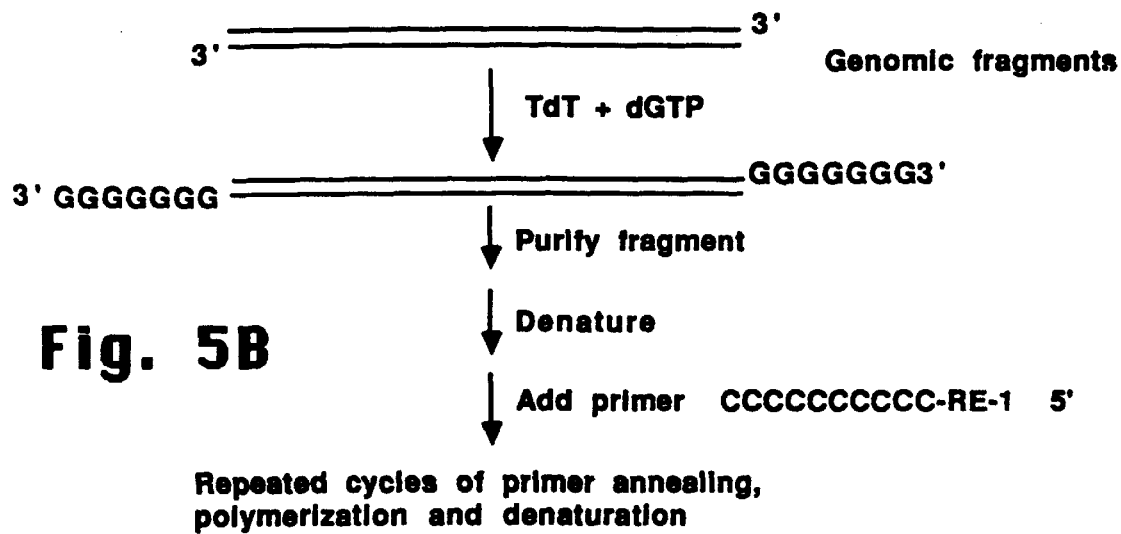
FIG. 5B is a modification of the FIG. 5B method.

FIG. 5B illustrates a modification of the duplex DNA amplification method just described. This method differs from the FIG. 5A method in that the duplex fragments are treated to produce homopolymer tailing, but are not subsequently ligated with a complementary homopolymer, to add 5'-end complementary sequences. Thus, in contrast to the basic method described herein, the present modification does not include the step of forming anti-sense strands with 5'-end common sequences.

After purification of the homopolymer tail fragments, the fragments are mixed with a homopolymer primer which is homologous to the fragment homopolymeric regions, a DNA polymerase, and all four dNTPs. Amplification is carried out by repeated denaturation, annealing and reaction with polymerase, as above. Since primed-strand replication is not expected to generate 3' homopolymeric ends, the newly synthesized fragments should not provide a template for further replication, and each round of replication should produce only a linear increase of the original duplex fragments with homopolymer tailing. Thus 25 rounds of replication should produce only about a 25 fold increase in fragment numbers. Surprisingly, experiments conducted in support of the present invention and described in Example 2, indicate that at least about a 200 fold increase in fragment concentration is achieved with 25 rounds of replication.

The amplification observed in the FIG. 5B method may be due to full-strand hybridization involving newly synthesized strands carrying 5'-end poly dC sequences (provided by the poly dC primer). It will be appreciated from the figure that such full-strand hybridization would yield duplex fragments having poly dC sequences at the opposite 5' ends of the two strands. The poly dC overhanging sequences in turn would provide a template for poly dG sequence formation on the adjoining 3' ends of the complementary strands, in the presence of the DNA polymerase and dGTP in the reaction mixture. The resulting fragments thus would have the same poly dG 3' ends and poly dC 5' ends as in the FIG. 5A embodiment, allowing fragment doubling with each replication cycle.

The fact that the actual amount of amplification observed is substantially less than the theoretical amplification presumably reflects the relatively small percentage of newly formed fragments which are able to hybridize with one another during the annealing step in the amplification reaction. This limitation could be overcome at least partially by allowing greater hybridization times in the early stages of the amplification reaction.

2. Random-Sequence Priming

Figure 6:
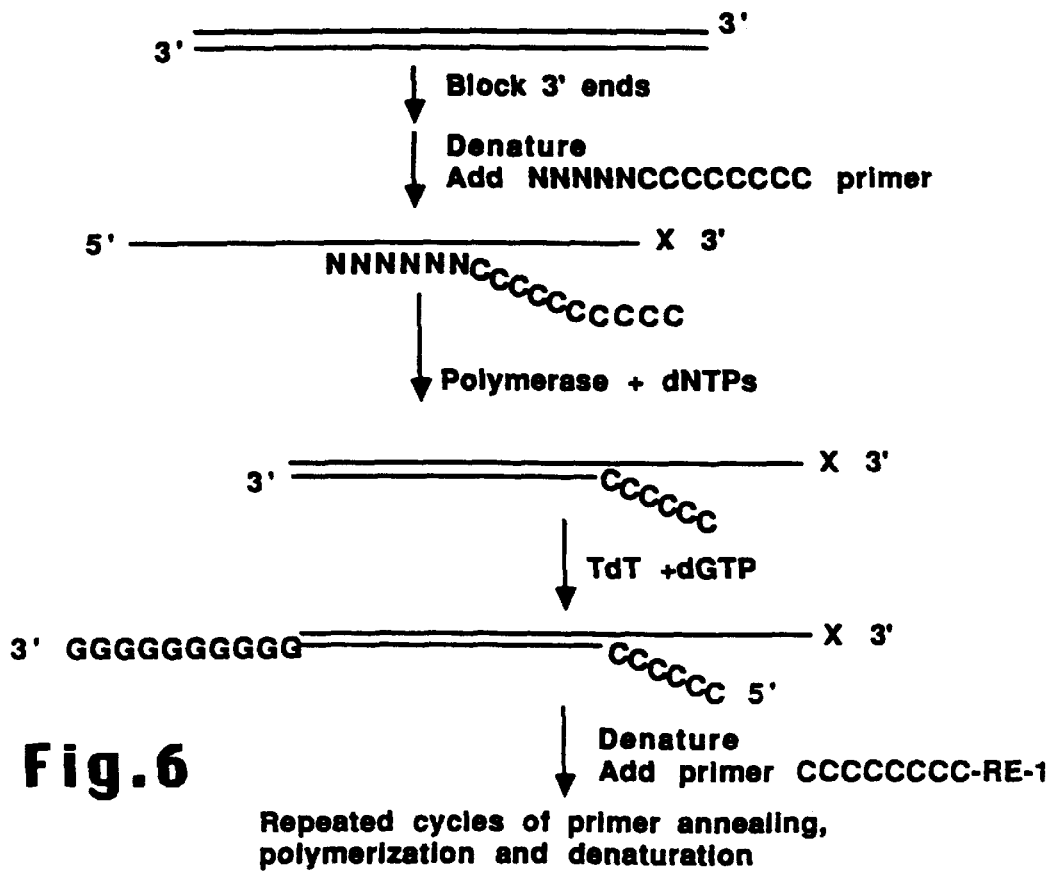
FIG. 6 is a flow diagram of a method for amplifying duplex DNA fragments according to another embodiment of the invention.

FIG. 6 illustrates a related method for duplex DNA amplification, for use particularly where the fragments are longer than about 3–8 kilobases, and where it is desired to amplify 5' region fragment sequences.

Figure 3:
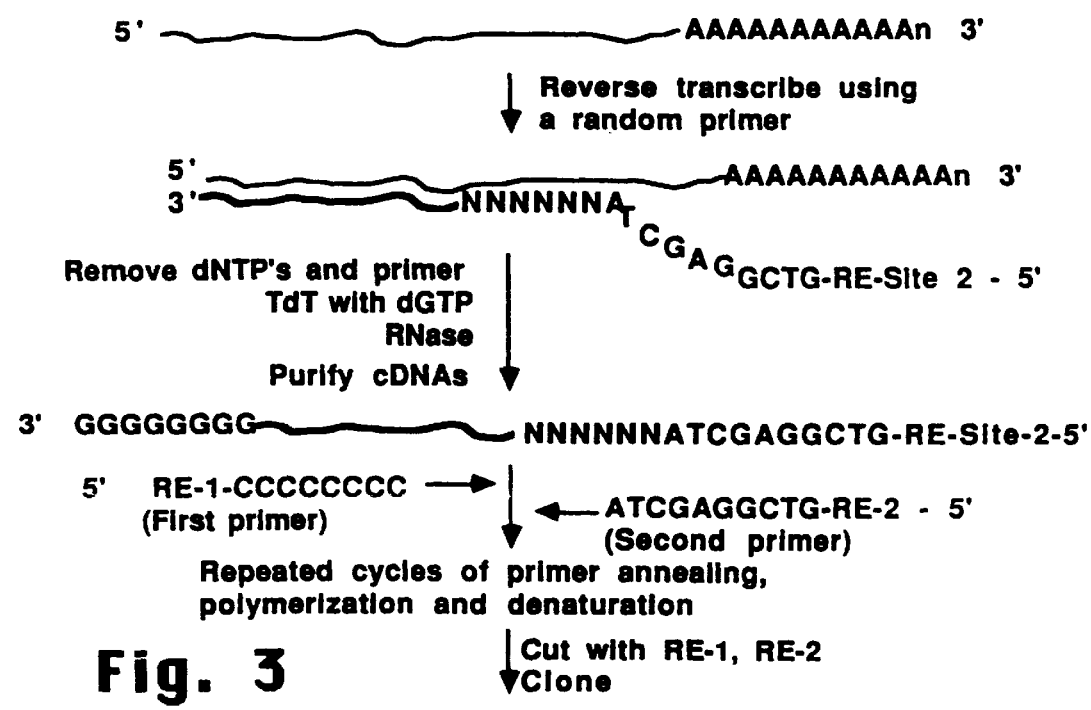
FIG. 3 is a flow diagram of a method for amplifying cDNA produced by random priming of poly A RNA.

The random primers which are employed preferably include 3'-end random sequences, as above, typically between about 4–8 bases long, a homopolymer region or other common-sequence region, the sequence of a selected restriction site, and protective bases, similar to the primer used in the FIG. 3 method.

In practicing the method, the duplex fragments are first treated to block the 3'-end OH groups of the duplex fragments. This insures that homopolymer tailing occurs only at the 3'-ends of newly synthesized (with random priming) DNA strands. Blocking of the 3' duplex ends may be carried out using T4 DNA polymerase and cordycepin triphosphate (3'-deoxy ATP) using conditions similar to those described in Maniatis (pp. 118–119) for repair of 3' DNA ends.

The fragments are then denatured by heating and mixed with a molar excess of the random primers. The primed fragments are copied with DNA polymerase and all four dNTPs, producing a new DNA strand having the random primer common sequence at its 5' end. This new strand is also referred to herein as an anti-sense strand, in analogy to first-strand cDNA synthesis.

After removing the polymerase and four dNTPs, the fragments are treated with TdT and a selected dNTP, to produce homopolymer tailing at newly synthesized strands in the duplex fragments, as indicated in the figure. In the method illustrated, where the first-strand primer includes a homopolymer binding region, such as poly dC, the homopolymer tail is complementary to the primer sequence, such as poly dG, allowing amplification with a single primer, in this case, a poly dC primer.

The duplex fragments are separated from the tailing components and added to an amplification reaction mixture which includes DNA polymerase, the above homopolymer primer (where the anti-sense strands have complementary homopolymer end regions, as in FIG. 6) and all four dNTPs. Repeated cycles of primer annealing, polymerization, and denaturation are carried out as above, until a desired degree of amplification is achieved. It will be appreciated how the method can be modified for amplification with different-sequence primers.

III. Utility

The amplification method of the invention is useful for RNA and DNA fragment amplification where limited amounts of fragment material are available, and for directional cloning of cDNA fragments. For example, where a relatively small amount of cellular or tissue material is available as an RNA source, the method allows for rapid amplification for purposes of cDNA cloning. The results shown in FIG. 7, and described in Example 1, indicate that mRNA from as few as $10^3$ cells may be detected after amplification. The results shown in FIG. 8, and also discussed in Example 1, demonstrate that for a specific gene sequence, such as interleukin-2 from human T cells, the method provides a rapid amplification of the RNA-derived fragments.

Using the two-primer approach described above, the amplified fragments can be prepared for directional cloning with different restriction site ends. The RNA amplification method also selects for full-copy sequences, since homopolymer tailing is poorly efficient with incomplete cDNA copying. A random primer method for DNA amplification allows for 5'-end sequence amplification, in the case of relatively long fragments.

Figure 10:
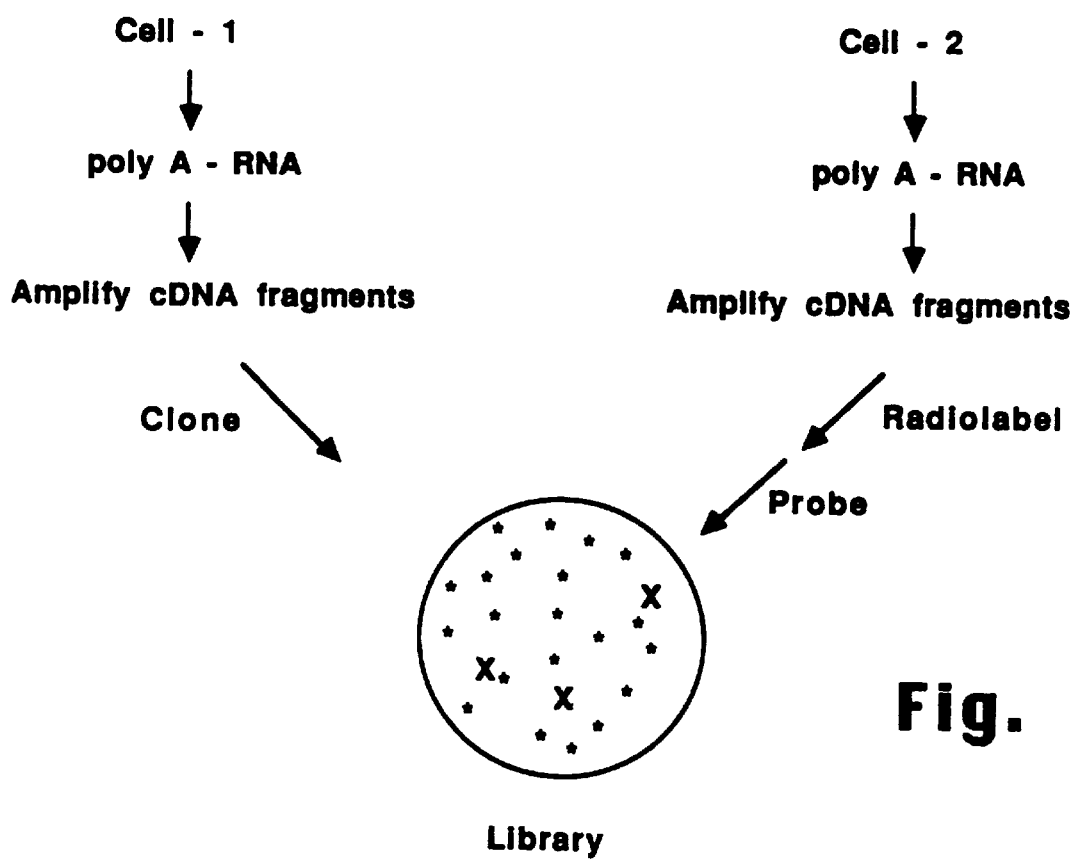
FIG. 10 illustrates an application of the method of the invention to identifying RNA species which are unique to one of two cell sources.

An application of the RNA amplification method for identifying RNA species which are unique to one of two related cell sources is illustrated in FIG. 10. The two cell sources may represent, for example, infected and non-infected cells, or normal and malignant cells, or activated and unactivated cells where it is desired to identify RNA species related specifically to cell infection or a malignant or activated cell state. RNA from the two cell sources is isolated and amplified as above, either by single- or dual-primer methods. The mixture of amplified fragments from the first source is cloned in a suitable cloning vector, to form a cloning fragment library, indicated at the bottom in the figure by a plate with many transformed host cells. The amplified mixture from the second source is radiolabeled, such as by nick translation or the like, for use as a probe against the library clones. Probe hybridization on a replica plate of the cloning vector library is performed conventionally by Southern blotting. The autoradiograph of the hybridized plate(s) is compared with the original library plate(s) to identify those library clones which are also common to the second source fragments. Species which are unique to the first source indicated by x's in the figure, are then identified.

The method can be applied to purified, enriched, or subfractionated DNA fragments, for increasing the amount of fragment material available for further processing, e.g., further enrichment. For example, in the above method for identifying unique sequences, the cloned unique sequence fragments can be isolated and further enriched by additional amplification and selection. As another example, a DNA subfraction obtained by gel electrophoresis can be amplified. Here the fragment mixture, prior to fractionation, is equipped with an end linker, and the selected fragment band is further isolated, either in situ within the gel, or after selective elution, by addition of primer, polymerase, and nucleotides, with repeated replication steps.

The following examples illustrate the method of fragment amplification and fragment isolation described above, but are in no way intended to limit the scope of the method or its applications.

Materials and Methods

Bluescript™ M13± was obtained from Stratagene (La Jolla, Calif.); and E. coli strain DH5 and E. coli strain JM101, from Bethesda Research Labs (Bethesda, Md.).

Terminal deoxynucleotide transferase (calf thymus), alkaline phosphatase (calf intestine), polynucleotide kinase, E. coli DNA polymerase I (Klenow fragment), and S1 nuclease were obtained from Boehringer Mannheim Biochemicals (Indianapolis, Ind.);

XbaI, XhoI, T4 DNA ligase and T4 DNA polymerase were obtained from New England Biolabs (Beverly, Mass.); and streptavidin agarose, from Bethesda Research Labs (Bethesda, Md.). Low-gelling temperature agarose (Sea Plaque) was obtained from FMC (Rockland, Me.). Nitrocellulose filters were obtained from Schleicher and Schuell (Natick, Mass.).

Synthetic oligonucleotide linkers and primers were prepared using commercially available automated oligonucleotide synthesizers. Alternatively, custom designed synthetic oligonucleotides may be purchased, for example, from Synthetic Genetics (San Diego, Calif.). cDNA synthesis kit and random priming labeling kits were obtained from Boehringer-Mannheim Biochemical (BMB, Indianapolis, Ind.).

Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7 pmoles gamma $^{32}$P-ATP (2.9 mCi/mmole), 0.1 mM spermidine, 0.1 mM EDTA.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 ug of plasmid or DNA sequence is cleaved by one unit of enzyme in about 20 ul of buffer solution after 1 hr digestion at 37° C.; in the examples herein, typically, an excess of restriction enzyme is used to insure complete digestion of the DNA substrate.

Incubation times of about one hour to two hours at about 37° C. are workable, although variations can be easily tolerated. After each incubation, protein is removed by extraction with phenol/chloroform, and may be followed by ether extraction, and the nucleic acid recovered from aqueous fractions by precipitation with ethanol (70%). If desired, size separation of the cleaved fragments may be performed by polyacrylamide gel or agarose gel electrophoresis using standard techniques. A general description of size separations is found in Methods in Enzymology (1980) 65:499–560.

Restriction cleaved fragments may be blunt ended by treating with the large fragment of E. coli DNA polymerase I (Klenow reagent) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1–1.0 mM dNTPs. The Klenow fragment fills in at 5' single-stranded overhangs in the presence of the four nucleotides. If desired, selective repair can be performed by supplying only one of the, or selected, dNTPs within the limitations dictated by the nature of the overhang. After treatment with Klenow reagent, the mixture is extracted with phenol/chloroform and ethanol precipitated. Treatment under appropriate conditions with S1 nuclease results in hydrolysis of any single-stranded portions of DNA. In particular, the nicking of 5' hairpins formed on synthesis of cDNA is achieved.

Blocking of 3' ends of DNA is carried out using T4 DNA polymerase and cordycepin triphosphate (3'-deoxy ATP) using conditions similar to those described by Maniatis (p. 118–119) for repair of 3' ends of DNA. Only cordycepin is used for repair.

Ligations are performed in 15–50 ul volumes under the following standard conditions and temperatures: for example, 20 mM Tris-Cl pH 7.5, 10 mM $MgCl_2$, 10 mM DTT, 33 mg/ml BSA, 10 mM-50 mM NaCl, and either 40 mM ATP, 0.01–0.02 (Weiss) units T4 DNA ligase at 14° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 mg/ml total DNA concentrations (5–100 nM total end concentration). Intermolecular blunt end ligations are performed at 1 mM total ends concentration.

In vector constructions employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit per mg of BAP at 60° C. for one hour or 1 unit of CIP per mg of vector at 37° C. for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

EXAMPLE 1

Full-length mRNA Amplification with Different-Sequence Primers

A. Preparing cDNA fragments

Human peripheral blood T cells were isolated from normal individuals by T rosetting, and total RNA was isolated from about $10^7$ cells according to standard procedures (Cathula). The total RNA preparation was fractionated by oligo dT chromatography, also according to known procedures (Maniatis, p. 211), yielding a poly A mRNA preparation. The final preparation was diluted to an RNA concentration of about 1 ug/ml.

Aliquots of the mRNA preparation corresponding approximately to the expected yield of $10^3$ cells (0.01 percent of the total mRNA isolate), $10^4$ cells (0.1 percent of the total RNA yield), and $10^5$ cells (1 percent of the total mRNA yield) were used for making first-strand cDNA, as described in the cDNA kit supplied by Boehringer-Mannheim.

The RNA/DNA complex was purified by sequential extraction with one volume of phenol/chloroform, followed by 2 volumes ethanol (5 ug of tRNA was added as carrier) precipitations using 0.5 volume of 7.5M NH$_4$OAc pH 7.0 and 2 volumes of ethanol. After centrifugation (10 min in microfuge at room temp; about 14K rpm) the pellet was completely desiccated in a speed vac to assure complete removal of the NH$_4$OAc which is known to inhibit terminal deoxynucleotide transferase (TdT).

Each of the three mixtures of double-strand material was resuspended in 0.050 ml of 0.2M K cacodylate (pH 7.2), 4 mM MgCl$_2$, 1 mM 2-mercaptoethanol, as provided by BRL, which contained a final concentration of 25 uM of dGTP. To initiate the reaction, 15 units of TdT (supplied by BRL) was added and the reaction was incubated for 30 min at 37° C. At the end of the reaction 10–20 ug of RNase A (supplied by Boehringer-Mannheim) was added to the reaction and incubated at 37° C. for an additional 30 min. At the conclusion of the RNase A reaction, the reaction mix was extracted with phenol/chloroform as above and 5–10 ug of tRNA was added as carrier before ethanol precipitation as described above was carried out. Alternatively, the sample may be precipitated without carrier and treated with RNase A after resuspending the samples.

B. Amplifying the cDNA fragments

To 100 ul of 10 mM Tris-Cl buffer, pH 8.3, containing 1.5 mM MgCl$_2$ (Buffer A) was added 100 ul of the above cDNA fragment mixture 2 uM of a primer having the sequence d(5'-GGTCTAGAC$_{20}$- 3'), 2 uM of a primer having the sequence 5'-GGCTCGAGT$_{20}$-3'), 200 uM (final concentration) each of dATP, dCTP, dGTP, and dTTP, and 5 units of *Thermus aguaticus* DNA polymerase (Taq polymerase). The reaction mixture was heated to 94° C. for 1 minute for denaturation, allowed to cool to 50° C. for 2 min for primer annealing, and then heated to 72° C. for 5–12 min to allow for primer extension by Taq polymerase. The replication reaction, involving successive heating, cooling, and polymerase reaction, was repeated an additional 25 times with the aid of a Perkin Elmer Cetus DNA thermal cycler.

C. Separation of Amplified fragments

Figure 7:
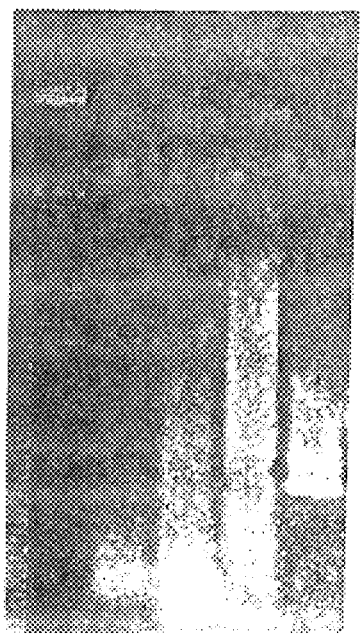
FIG. 7 shows gels of ethidium bromide-stained amplified duplex fragments, corresponding to the amount of material originally obtained from $10^3$ (lane 2), $10^4$ (lane 3), and $10^5$ (lane 4) cells.

Ten percent aliquots of the amplified DNA fragments in each of the three mixtures were applied to a 1.5% w/v agarose gel and electrophoresis was performed under standard conditions. The gels were stained with ethidium bromide and transferred to nitrocellulose filters for Southern blotting. FIG. 7 shows a picture of ethidium bromide staining of the amplified DNA. The three sample lanes (2, 3 and 4) in the gel are the samples corresponding to RNA from $10^3$, $10^4$, and $10^5$, as indicated. As seen, amplified DNA was obtained from the RNA samples corresponding to all three cell mixtures, although the band for $10^3$ cells was faint.

Lane 1 in FIG. 7 shows lambda phage size marker DNA fragments, and lane 5, a 10% sample of amplified control cDNA.

Figure 8:
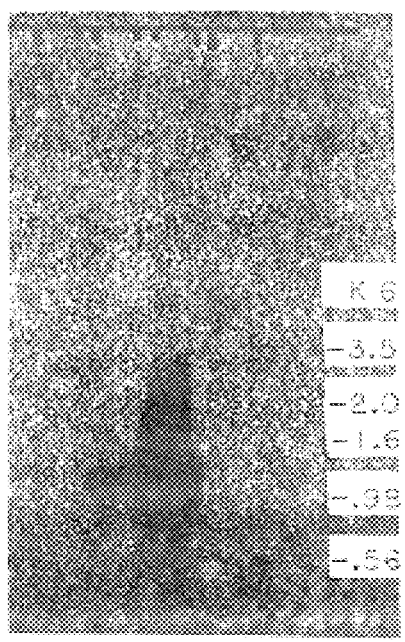
FIG. 8 shows Southern blots of the duplex fragments in gel lanes 2–4 from FIG. 7, hybridized with a radiolabeled probe made from the human interleukin-2 gene.

The three sample bands were transferred to nitrocellulose filters and hybridized with a radiolabeled probe which is homologous to the human interleukin-2 gene which is known to be present in T cells. The RNA transcript of this gene would therefore be expected in the RNA obtained from T cells which is to be amplified. The radiolabel pattern observed is shown in FIG. 8. As seen, the lanes corresponding to RNA from $10^4$ and $10^5$ (lanes 2 and 3) cells both contain easily detectable levels of cDNAs corresponding to the interleukin-2 gene.

D. Cloning amplified fragments

The amplified fragments from the sample mixture corresponding to $10^5$ cells are digested with XbaI and XhoI. Bluescript™ M13 plasmid is treated with the same enzymes, fractionated by electrophoresis to remove the small XhoI/XbaI fragment, and treated with alkaline phosphatase, prior to mixing with the above XbaI/XhoI fragments. Ligation is performed under conditions which promote circularization of the single plasmid fragments. The circularized plasmid is selected on *E. coli* strain DH5, and successful recombinants are selected for ampicillin resistance.

EXAMPLE 2

Full-Length DNA Amplification with Different-Sequence Primers

HaeIII-digested phiX174 DNA fragments were obtained from ProMega Biotech. The addition of poly dG tails was carried out in a 50 ul reaction containing 500 ng of fragments, 25 uM of dGTP, 15 to 30 units of TdT in buffer for 30 min at 37° C. At the conclusion of the reaction the sample was extracted with phenol/chloroform and precipitated with ethanol as in Example 1.

The DNA was amplified by adding 1 to 100 ng of DNA to a reaction mixture that contained 1 uM of poly dC primer and the same components as described in Example 1. The reaction cycle times were as described in Example 1 and a total of 25 cycles were performed.

Figure 9:
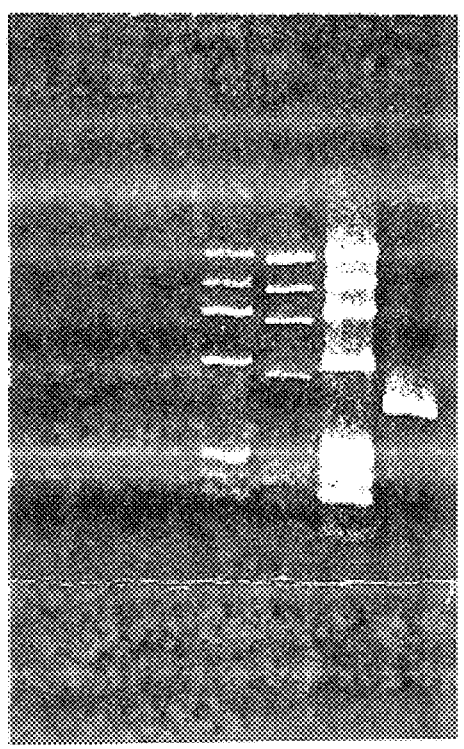
FIG. 9 is an autoradiograph of phiX174 duplex DNA fragments which were amplified by a one-primer-end amplification method.

FIG. 9 shows 2% agar gel electrophoresis patterns of non-amplified (lanes 1, 3 and 5) and corresponding amplified (lanes 2, 4 and 6) fragments stained with ethidium bromide. Lanes 1, 3 and 5 represent 1 ng, 10 ng and 100 ng, respectively, of fragment material. Lanes 2, 4 and 6 represent 10% of a two primer amplification of 1 ng, 10 ng and 100 ng fragment material, respectively. The results indicate a more than 200 fold amplification.

While the invention has been described with reference to particular embodiments, methods, construction and use, it will be apparent to those skilled in the art that various changes and modifications can be made without departing from the invention.

It is claimed:

1. A method of amplifying a mixture of different-sequence double-stranded DNA fragments, comprising treating the DNA fragments with terminal deoxynucleotide transferase and a selected deoxynucleotide triphosphate, to add a homopolymeric sequence to the 3' ends of both DNA fragment strands, mixing the DNA fragments containing the homopolymeric sequence with (i) a homopolymer primer that is complementary to said homopolymeric sequence, (ii) heat-stable DNA polymerase and (iii) all four deoxynucleotide triphosphates, heat denaturing the DNA fragment strands, annealing the mixture under conditions to form DNA fragment/primer duplexes, reacting the mixture under conditions in which the DNA fragment/primer duplexes are converted to double-stranded DNA molecules, repeating said denaturing, annealing, and reacting steps until a desired degree of fragment amplification has been achieved.

2. The method of claim 1, wherein said treating further includes ligating a complementary primer to the 5' ends of both DNA fragment strands forming 5' common sequence ends, where said complementary primer is complementary to the homopolymeric sequence and can serve both as the homopolymer primer and a 5'-end common sequence primer.

3. The method of claim 1, for use in amplifying double-stranded DNA fragments:
  (i) wherein said treating further includes,
    (a) denaturing the double-stranded DNA fragments to yield single-strands,
    (b) adding random primers, where said random primers contain (i) at their 3' end, random sequences effective to bind to complementary sequences of the DNA single-strands, and (ii) at their 5' ends, a common sequence, and
    (c) annealing the mixture under conditions to form DNA single-strand/random primer duplexes, reacting the mixture under conditions in which the DNA single-strand/random primer duplexes are converted to double-stranded DNA molecules; and
  (ii) where said mixing further includes a common sequence primer, where the sequence of the common sequence primer is the same as said common sequence.

4. The method of claim 3, where said treating further includes, protecting the 3'-ends of the duplex DNA fragments prior to said denaturing, to prevent homopolymer tailing of the original duplex fragments.

5. The method of claim 3, wherein the 5' common sequence and the 3' homopolymer sequence are complementary and, in said mixing, the common sequence primer and the homopolymer primer have the same sequence.

6. A method of amplifying a mixture of different-sequence nucleic acid fragment strands, comprising
  manipulating the nucleic acid fragment strands to form a mixture of different sequence DNA fragment strands, where each DNA fragment strand has a 3'-end and further contains a 5'-end common sequence,
  treating the DNA fragment strands with terminal deoxynucleotide transferase and a selected triphosphate, to add a homopolymeric sequence to the 3' ends,
  mixing the DNA fragment strands containing the homopolymeric sequence with (i) a homopolymer primer that is complementary to said homopolymeric sequence, (ii) a common-sequence primer that has the same sequence as said common sequence, (iii) heat-stable DNA polymerase and (iv) all four deoxynucleotide triphosphates,
  heat denaturing the DNA fragment strands,
  annealing the mixture under conditions to form DNA fragment strand/primer duplexes,
  reacting the mixture under conditions in which the DNA fragment strand/primer duplexes are converted to double-stranded DNA molecules,
  repeating said denaturing, annealing, and reacting, until a desired degree of fragment amplification has been achieved.

7. The method of claim 6, wherein said manipulating includes (a) adding an oligo dT primer to a mixture of poly A RNA species and (b) transcribing the RNA in the presence of the oligo dT primer, reverse transcriptase, and all four deoxynucleotide triphosphates, wherein said 5'-end common sequence is the poly dT sequence.

8. The method of claim 7, wherein the homopolymeric region of the DNA fragment strands is non-complementary to said 5' poly dT common sequence.

9. The method of claim 8, for use in constructing a library of amplified double-stranded DNA inserts in a cloning vector and where the library construction further includes inserting the double-stranded DNA fragments in the vector between the DNA-insert sites.

10. The method of claim 7, wherein said homopolymeric sequence is a poly A sequence and in said mixing the common sequence primer and the homopolymer primer both contain poly dT sequences.

11. The method of claim 6, wherein said manipulating further includes
  (a) isolating a mixture of RNA species,
  (b) adding random primers having (i) at their 3' ends, random sequences effective to bind to complementary RNA sequences in the RNA species mixture, and (ii) at their 5' ends, said 5'-end common sequence, and
  (c) under priming conditions, reacting the RNA species and attached random primers with reverse transcriptase and all four deoxynucleotide triphosphates, under conditions which produce DNA fragment strand copies of the RNA.

12. The method of claim 11, wherein the mixture of RNA species comprises RNA molecules of greater than about 3–8 kilobases in size.

13. The method of claim 11, wherein the 5' common sequence and the 3' homopolymer sequence are complementary and, in said mixing, the common sequence primer and the homopolymer primer have the same sequence.

14. The method of claim 11, wherein the 5' common sequence and the 3' homopolymer sequence are non-complementary and said homopolymer primer and common-sequence primer each have different 5'-end sequences.

15. A method of preparing a mixture of single-stranded RNA fragments for cloning in a cloning vector, comprising
  transcribing the RNA fragments to an RNA/DNA complex using an RNA-strand primer, where said RNA-strand primer (i) has a sequence complementary to a 3' sequence of the RNA fragments and (ii) is effective to produce in the resulting RNA/DNA duplex DNA fragment strands having a selected common 5'-end sequence,
  treating the DNA fragment strands with terminal deoxynucleotide transferase in the presence of a selected deoxynucleotide, to form a homopolymeric sequence at the 3'-end of the DNA fragment strands,
  mixing the DNA fragment strands containing the homopolymeric sequence with (i) a homopolymer primer having a binding sequence which is complementary to the 3'-end homopolymeric sequence of the DNA fragment strands, (ii) a common-sequence primer which has the same sequence as said selected common 5'-end sequence, (iii) a heat-stable DNA polymerase and (iv) all four deoxynucleotide triphosphates,
  heat denaturing the DNA fragment strands,
  annealing the mixture under conditions to form DNA fragment stand/primer duplexes,
  reacting the mixture under conditions in which the DNA fragment strand/primer duplexes are converted to double-stranded DNA molecules,
  repeating said denaturing, annealing, and reacting steps until a desired degree of fragment amplification has been achieved.

16. The method of claim 15, wherein said RNA fragments are poly A RNAs, and said common-sequence primer includes a poly dT sequence.

17. The method of claim 15, wherein said transcribing is carried out with random primers having (i) at their 3' ends, random sequences effective to bind to complementary sequences of RNA fragments, and (ii) at their 5' ends, said 5'-end common sequence.

* * * * *